(12) United States Patent
Pav

(10) Patent No.: US 8,437,822 B2
(45) Date of Patent: May 7, 2013

(54) SYSTEM AND METHOD FOR ESTIMATING BLOOD ANALYTE CONCENTRATION

(75) Inventor: Steven E. Pav, San Francisco, CA (US)

(73) Assignee: Covidien LP, Mansfield, MA (US)

( * ) Notice: Subject to any disclaimer, the term of this patent is extended or adjusted under 35 U.S.C. 154(b) by 1076 days.

(21) Appl. No.: 12/412,978

(22) Filed: Mar. 27, 2009

(65) Prior Publication Data

US 2009/0247845 A1    Oct. 1, 2009

Related U.S. Application Data

(60) Provisional application No. 61/072,293, filed on Mar. 28, 2008.

(51) Int. Cl.
*A61B 5/1455* (2006.01)

(52) U.S. Cl.
USPC ........................................................ 600/322

(58) Field of Classification Search .............. 600/310, 600/322
See application file for complete search history.

(56) References Cited

U.S. PATENT DOCUMENTS

| | | |
|---|---|---|
| 3,638,640 A | 2/1972 | Shaw |
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |

(Continued)

FOREIGN PATENT DOCUMENTS

| | | |
|---|---|---|
| DE | 19632361 | 2/1997 |
| DE | 69123448 | 5/1997 |

(Continued)

OTHER PUBLICATIONS

Ogawa et al. "Support Vector Machines as Multivariate Calibration Model for Prediction of Blood Glucose Concentration Using New Non-invasive Optical Method Named Pulse Glucometry" Proceedings of the 29th Annual International Conference of the IEEE EMBS Cite Internationale, Lyon, France Aug. 23-26, 2007.*

(Continued)

*Primary Examiner* — Sean P Dougherty
*Assistant Examiner* — Michael C Stout

(57) ABSTRACT

There is provided a system and method for estimating blood analyte concentration using a non-invasive medical device. The method includes detecting light from a plurality of light sources and generating signals representative of observed absorption of the light from the plurality of light sources. Blood analyte concentrations are then estimated using support vector regression analysis.

20 Claims, 5 Drawing Sheets

U.S. PATENT DOCUMENTS

| | | |
|---|---|---|
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |

| Patent No. | Date | Inventor |
|---|---|---|
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | Delonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,758 A | 7/1998 | Ausec et al. |
| 5,786,592 A | 7/1998 | Hök |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,182 A | 10/1998 | Raley et al. |
| 5,830,135 A | 11/1998 | Bosque et al. |
| 5,830,136 A | 11/1998 | DeLonzor et al. |
| 5,830,137 A | 11/1998 | Scharf |
| 5,830,139 A | 11/1998 | Abreu |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,871,442 A | 2/1999 | Madarasz et al. |
| 5,873,821 A | 2/1999 | Chance et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |

| | | | | | | |
|---|---|---|---|---|---|---|
| 5,912,656 | A | 6/1999 | Tham et al. | 6,151,518 A | 11/2000 | Hayashi |
| 5,913,819 | A | 6/1999 | Taylor et al. | 6,152,754 A | 11/2000 | Gerhardt et al. |
| 5,916,154 | A | 6/1999 | Hobbs et al. | 6,154,667 A | 11/2000 | Miura et al. |
| 5,916,155 | A | 6/1999 | Levinson et al. | 6,157,850 A | 12/2000 | Diab et al. |
| 5,919,133 | A | 7/1999 | Taylor et al. | 6,163,715 A | 12/2000 | Larsen et al. |
| 5,919,134 | A | 7/1999 | Diab | 6,165,005 A | 12/2000 | Mills et al. |
| 5,920,263 | A | 7/1999 | Huttenhoff et al. | 6,173,196 B1 | 1/2001 | Delonzor et al. |
| 5,921,921 | A | 7/1999 | Potratz et al. | 6,178,343 B1 | 1/2001 | Bindszus et al. |
| 5,922,607 | A | 7/1999 | Bernreuter | 6,181,958 B1 | 1/2001 | Steuer et al. |
| 5,924,979 | A | 7/1999 | Swedlow et al. | 6,181,959 B1 | 1/2001 | Schöllermann et al. |
| 5,924,980 | A | 7/1999 | Coetzee | 6,184,521 B1 | 2/2001 | Coffin, IV et al. |
| 5,924,982 | A | 7/1999 | Chin | 6,188,470 B1 | 2/2001 | Grace |
| 5,924,985 | A | 7/1999 | Jones | 6,192,260 B1 | 2/2001 | Chance |
| 5,934,277 | A | 8/1999 | Mortz | 6,195,575 B1 | 2/2001 | Levinson |
| 5,934,925 | A | 8/1999 | Tobler et al. | 6,198,951 B1 | 3/2001 | Kosuda et al. |
| 5,940,182 | A | 8/1999 | Lepper, Jr. et al. | 6,206,830 B1 | 3/2001 | Diab et al. |
| 5,954,644 | A | 9/1999 | Dettling et al. | 6,213,952 B1 | 4/2001 | Finarov et al. |
| 5,960,610 | A | 10/1999 | Levinson et al. | 6,217,523 B1 | 4/2001 | Amano et al. |
| 5,961,450 | A | 10/1999 | Merchant et al. | 6,222,189 B1 | 4/2001 | Misner et al. |
| 5,961,452 | A | 10/1999 | Chung et al. | 6,226,539 B1 | 5/2001 | Potratz |
| 5,964,701 | A | 10/1999 | Asada et al. | 6,226,540 B1 | 5/2001 | Bernreuter et al. |
| 5,971,930 | A | 10/1999 | Elghazzawi | 6,229,856 B1 | 5/2001 | Diab et al. |
| 5,978,691 | A | 11/1999 | Mills | 6,230,035 B1 | 5/2001 | Aoyagi et al. |
| 5,978,693 | A | 11/1999 | Hamilton et al. | 6,233,470 B1 | 5/2001 | Tsuchiya |
| 5,983,122 | A | 11/1999 | Jarman et al. | 6,236,871 B1 | 5/2001 | Tsuchiya |
| 5,987,343 | A | 11/1999 | Kinast | 6,236,872 B1 | 5/2001 | Diab et al. |
| 5,991,648 | A | 11/1999 | Levin | 6,240,305 B1 | 5/2001 | Tsuchiya |
| 5,995,855 | A | 11/1999 | Kiani et al. | 6,253,097 B1 | 6/2001 | Aronow et al. |
| 5,995,856 | A | 11/1999 | Mannheimer et al. | 6,253,098 B1 | 6/2001 | Walker et al. |
| 5,995,858 | A | 11/1999 | Kinast | 6,256,523 B1 | 7/2001 | Diab et al. |
| 5,995,859 | A | 11/1999 | Takahashi | 6,256,524 B1 | 7/2001 | Walker et al. |
| 5,997,343 | A | 12/1999 | Mills et al. | 6,261,236 B1 | 7/2001 | Grimblatov |
| 5,999,834 | A | 12/1999 | Wang et al. | 6,263,221 B1 | 7/2001 | Chance et al. |
| 6,002,952 | A | 12/1999 | Diab et al. | 6,263,222 B1 | 7/2001 | Diab et al. |
| 6,005,658 | A | 12/1999 | Kaluza et al. | 6,263,223 B1 | 7/2001 | Shepherd et al. |
| 6,006,120 | A | 12/1999 | Levin | 6,266,546 B1 | 7/2001 | Steuer et al. |
| 6,011,985 | A | 1/2000 | Athan et al. | 6,266,547 B1 | 7/2001 | Walker et al. |
| 6,011,986 | A | 1/2000 | Diab et al. | 6,272,363 B1 | 8/2001 | Casciani et al. |
| 6,014,576 | A | 1/2000 | Raley et al. | 6,278,522 B1 | 8/2001 | Lepper, Jr. et al. |
| 6,018,673 | A | 1/2000 | Chin et al. | 6,280,213 B1 | 8/2001 | Tobler et al. |
| 6,018,674 | A | 1/2000 | Aronow | 6,280,381 B1 | 8/2001 | Malin et al. |
| 6,022,321 | A | 2/2000 | Amano et al. | 6,285,894 B1 | 9/2001 | Oppelt et al. |
| 6,023,541 | A | 2/2000 | Merchant et al. | 6,285,895 B1 | 9/2001 | Ristolainen et al. |
| 6,026,312 | A | 2/2000 | Shemwell et al. | 6,285,896 B1 | 9/2001 | Tobler et al. |
| 6,026,314 | A | 2/2000 | Amerov et al. | 6,298,252 B1 | 10/2001 | Kovach et al. |
| 6,031,603 | A | 2/2000 | Fine et al. | 6,308,089 B1 | 10/2001 | Von der Ruhr et al. |
| 6,035,223 | A | 3/2000 | Baker, Jr. | 6,312,393 B1 | 11/2001 | Abreu |
| 6,036,642 | A | 3/2000 | Diab et al. | 6,321,100 B1 | 11/2001 | Parker |
| 6,041,247 | A | 3/2000 | Weckstrom et al. | 6,330,468 B1 | 12/2001 | Scharf |
| 6,044,283 | A | 3/2000 | Fein et al. | 6,334,065 B1 | 12/2001 | Al-Ali et al. |
| 6,047,201 | A | 4/2000 | Jackson, III | 6,339,715 B1 | 1/2002 | Bahr et al. |
| 6,061,584 | A | 5/2000 | Lovejoy et al. | 6,343,223 B1 | 1/2002 | Chin et al. |
| 6,064,898 | A | 5/2000 | Aldrich | 6,343,224 B1 | 1/2002 | Parker |
| 6,064,899 | A | 5/2000 | Fein et al. | 6,349,228 B1 | 2/2002 | Kiani et al. |
| 6,067,462 | A | 5/2000 | Diab et al. | 6,351,658 B1 | 2/2002 | Middleman et al. |
| 6,073,038 | A | 6/2000 | Wang et al. | 6,353,750 B1 | 3/2002 | Kimura et al. |
| 6,078,833 | A | 6/2000 | Hueber | 6,356,774 B1 | 3/2002 | Bernstein et al. |
| 6,081,735 | A | 6/2000 | Diab et al. | 6,360,113 B1 | 3/2002 | Dettling |
| 6,081,742 | A | 6/2000 | Amano et al. | 6,360,114 B1 | 3/2002 | Diab et al. |
| 6,083,157 | A | 7/2000 | Noller | 6,361,501 B1 | 3/2002 | Amano et al. |
| 6,083,172 | A | 7/2000 | Baker, Jr. et al. | 6,363,269 B1 | 3/2002 | Hanna et al. |
| 6,088,607 | A | 7/2000 | Diab et al. | 6,370,408 B1 | 4/2002 | Merchant et al. |
| 6,094,592 | A | 7/2000 | Yorkey et al. | 6,370,409 B1 | 4/2002 | Chung et al. |
| 6,095,974 | A | 8/2000 | Shemwell et al. | 6,374,129 B1 | 4/2002 | Chin et al. |
| 6,104,938 | A | 8/2000 | Huiku et al. | 6,377,829 B1 | 4/2002 | Al-Ali et al. |
| 6,112,107 | A | 8/2000 | Hannula | 6,381,479 B1 | 4/2002 | Norris |
| 6,113,541 | A | 9/2000 | Dias et al. | 6,381,480 B1 | 4/2002 | Stoddar et al. |
| 6,115,621 | A | 9/2000 | Chin | 6,385,471 B1 | 5/2002 | Mortz |
| 6,120,460 | A | 9/2000 | Abreu | 6,385,821 B1 | 5/2002 | Modgil et al. |
| 6,122,535 | A | 9/2000 | Kaestle et al. | 6,388,240 B2 | 5/2002 | Schulz et al. |
| 6,133,994 | A | 10/2000 | Mathews et al. | 6,393,310 B1 | 5/2002 | Kuenster |
| 6,134,460 | A | 10/2000 | Chance | 6,397,091 B2 | 5/2002 | Diab et al. |
| 6,135,952 | A | 10/2000 | Coetzee | 6,397,092 B1 | 5/2002 | Norris et al. |
| 6,144,444 | A | 11/2000 | Haworth et al. | 6,397,093 B1 | 5/2002 | Aldrich |
| 6,144,867 | A | 11/2000 | Walker et al. | 6,400,971 B1 | 6/2002 | Finarov et al. |
| 6,144,868 | A | 11/2000 | Parker | 6,400,972 B1 | 6/2002 | Fine |
| 6,149,481 | A | 11/2000 | Wang et al. | 6,402,690 B1 | 6/2002 | Rhee et al. |
| 6,150,951 | A | 11/2000 | Olejniczak | 6,408,198 B1 | 6/2002 | Hanna et al. |
| 6,151,107 | A | 11/2000 | Schöllermann et al. | 6,411,832 B1 | 6/2002 | Guthermann |

| | | |
|---|---|---|
| 6,411,833 B1 | 6/2002 | Baker, Jr. et al. |
| 6,415,236 B2 | 7/2002 | Kobayashi et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,487,439 B1 | 11/2002 | Skladnev et al. |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,544,193 B2 | 4/2003 | Abreu |
| 6,546,267 B1 | 4/2003 | Sugiura et al. |
| 6,549,795 B1 | 4/2003 | Chance |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,622,095 B2 | 9/2003 | Kobayashi et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,690,958 B1 | 2/2004 | Walker et al. |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,048 B1 | 3/2004 | Chance |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,785,568 B2 | 8/2004 | Chance |
| 6,792,300 B1 | 9/2004 | Diab et al. |
| 6,793,654 B2 | 9/2004 | Lemberg |

| Patent Number | Date | Inventor |
|---|---|---|
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,873,865 B2 | 3/2005 | Steuer et al. |
| 6,879,850 B2 | 4/2005 | Kimball |
| 6,882,874 B2 | 4/2005 | Huiku |
| 6,889,153 B2 | 5/2005 | Dietiker |
| 6,896,661 B2 | 5/2005 | Dekker et al. |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,949,081 B1 | 9/2005 | Chance |
| 6,950,687 B2 | 9/2005 | Al-Ali |
| 6,961,598 B2 | 11/2005 | Diab |
| 6,963,767 B2 | 11/2005 | Rantala et al. |
| 6,970,792 B1 | 11/2005 | Diab |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,365 B1 | 1/2006 | Parker et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,001,337 B2 | 2/2006 | Dekker et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,044,918 B2 | 5/2006 | Diab |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,079,880 B2 | 7/2006 | Stetson |
| 7,085,597 B2 | 8/2006 | Fein et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,187,962 B2 | 3/2007 | Shingo |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,215,984 B2 | 5/2007 | Diab et al. |
| 7,215,986 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,432 B2 | 8/2007 | Fine |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Scmid |
| 7,280,858 B2 | 10/2007 | Al-Ali et al. |
| 7,283,242 B2 | 10/2007 | Thornton |
| 7,295,866 B2 | 11/2007 | Al-Ali et al. |
| 7,302,284 B2 | 11/2007 | Baker, Jr. et al. |
| 7,305,262 B2 | 12/2007 | Brodnick et al. |
| 7,315,753 B2 | 1/2008 | Baker, Jr. et al. |
| 7,328,053 B1 | 2/2008 | Diab et al. |
| 7,333,842 B2 | 2/2008 | Schweitzer et al. |
| 7,336,982 B2 | 2/2008 | Yoo |
| 7,336,983 B2 | 2/2008 | Baker, Jr. et al. |
| 7,373,194 B2 | 5/2008 | Weber et al. |
| 7,376,453 B1 | 5/2008 | Diab et al. |
| 7,377,899 B2 | 5/2008 | Weber et al. |
| 7,383,070 B2 | 6/2008 | Diab et al. |
| 7,403,806 B2 | 7/2008 | Norris |
| 7,440,787 B2 | 10/2008 | Diab |
| 7,672,497 B2 * | 3/2010 | Nicponski ............... 382/128 |
| 8,160,668 B2 * | 4/2012 | Pav ............... 600/323 |
| 2001/0005773 A1 | 6/2001 | Larsen et al. |
| 2001/0020122 A1 | 9/2001 | Steuer et al. |
| 2001/0021803 A1 | 9/2001 | Blank et al. |
| 2001/0039376 A1 | 11/2001 | Steuer et al. |
| 2001/0044700 A1 | 11/2001 | Kobayashi et al. |
| 2001/0051767 A1 | 12/2001 | Williams et al. |
| 2002/0026106 A1 | 2/2002 | Khalil et al. |
| 2002/0026109 A1 | 2/2002 | Diab et al. |
| 2002/0028990 A1 | 3/2002 | Sheperd et al. |
| 2002/0035318 A1 | 3/2002 | Mannheimer et al. |
| 2002/0038078 A1 | 3/2002 | Ito |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0068859 A1 | 6/2002 | Knopp |
| 2002/0111748 A1 | 8/2002 | Kobayashi et al. |
| 2002/0128544 A1 | 9/2002 | Diab et al. |
| 2002/0133067 A1 | 9/2002 | Jackson, III |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2002/0198443 A1 | 12/2002 | Ting |
| 2003/0018243 A1 | 1/2003 | Gerhardt et al. |
| 2003/0023140 A1 | 1/2003 | Chance |
| 2003/0036690 A1 | 2/2003 | Geddes et al. |
| 2003/0045785 A1 | 3/2003 | Diab et al. |

| Publication | Date | Inventor |
|---|---|---|
| 2003/0055324 A1 | 3/2003 | Wasserman |
| 2003/0060693 A1 | 3/2003 | Monfre et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0139687 A1 | 7/2003 | Abreu |
| 2003/0144584 A1 | 7/2003 | Mendelson |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0220548 A1 | 11/2003 | Schmitt |
| 2003/0220576 A1 | 11/2003 | Diab |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054270 A1 | 3/2004 | Pewzner et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0127779 A1 | 7/2004 | Steuer et al. |
| 2004/0133081 A1* | 7/2004 | Teller et al. .................. 600/300 |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0171920 A1 | 9/2004 | Mannheimer et al. |
| 2004/0171948 A1 | 9/2004 | Terry |
| 2004/0176670 A1 | 9/2004 | Takamura et al. |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230106 A1 | 11/2004 | Schmitt et al. |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0075550 A1 | 4/2005 | Lindekugel |
| 2005/0080323 A1 | 4/2005 | Kato |
| 2005/0101850 A1 | 5/2005 | Parker |
| 2005/0113656 A1 | 5/2005 | Chance |
| 2005/0143634 A1 | 6/2005 | Baker, Jr. et al. |
| 2005/0168722 A1 | 8/2005 | Forstner et al. |
| 2005/0177034 A1 | 8/2005 | Beaumont |
| 2005/0180497 A1 | 8/2005 | Tanaka et al. |
| 2005/0192488 A1 | 9/2005 | Bryenton et al. |
| 2005/0192493 A1 | 9/2005 | Wuori |
| 2005/0197548 A1 | 9/2005 | Dietiker |
| 2005/0203357 A1 | 9/2005 | Debreczeny et al. |
| 2005/0209517 A1 | 9/2005 | Diab et al. |
| 2005/0216426 A1* | 9/2005 | Weston et al. .................. 706/12 |
| 2005/0228248 A1 | 10/2005 | Dietiker |
| 2005/0250998 A1 | 11/2005 | Huiku |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0025660 A1 | 2/2006 | Swedlow et al. |
| 2006/0030763 A1 | 2/2006 | Mannheimer et al. |
| 2006/0052680 A1 | 3/2006 | Diab |
| 2006/0058594 A1 | 3/2006 | Ishizuka et al. |
| 2006/0058683 A1 | 3/2006 | Chance |
| 2006/0064024 A1 | 3/2006 | Schnall |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0195028 A1 | 8/2006 | Hannula et al. |
| 2006/0200014 A1 | 9/2006 | Fine et al. |
| 2006/0200016 A1 | 9/2006 | Diab et al. |
| 2006/0206021 A1 | 9/2006 | Diab |
| 2006/0217609 A1 | 9/2006 | Diab et al. |
| 2006/0224058 A1 | 10/2006 | Mannheimer |
| 2006/0247501 A1 | 11/2006 | Ali |
| 2006/0247532 A1* | 11/2006 | Ramanujam et al. ......... 600/476 |
| 2006/0258921 A1 | 11/2006 | Addison et al. |
| 2006/0269161 A1* | 11/2006 | Ramsay et al. ............... 382/276 |
| 2006/0287587 A1 | 12/2006 | Yarita |
| 2006/0287588 A1 | 12/2006 | Yarita |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0043281 A1* | 2/2007 | Fine ............................. 600/335 |
| 2007/0049811 A1 | 3/2007 | Kobayashi et al. |
| 2007/0073126 A1 | 3/2007 | Raridan, Jr. |
| 2007/0225581 A1 | 9/2007 | Diab et al. |
| 2007/0249918 A1 | 10/2007 | Diab et al. |
| 2007/0291832 A1 | 12/2007 | Diab et al. |
| 2008/0004514 A1 | 1/2008 | Diab et al. |
| 2008/0033266 A1 | 2/2008 | Diab et al. |
| 2008/0036752 A1 | 2/2008 | Diab et al. |
| 2008/0045823 A1 | 2/2008 | Diab et al. |
| 2008/0081974 A1* | 4/2008 | Pav ............................. 600/336 |
| 2008/0137066 A1 | 6/2008 | Weinstein et al. |
| 2008/0194925 A1 | 8/2008 | Alsafadi et al. |
| 2008/0232667 A1* | 9/2008 | Kitamura et al. ............. 382/132 |

| | | | |
|---|---|---|---|
| 2008/0233576 | A1* | 9/2008 | Weston et al. ............... 435/6 |
| 2008/0249393 | A1 | 10/2008 | Finarov et al. |
| 2009/0010521 | A1* | 1/2009 | Ramsay et al. ............ 382/141 |

FOREIGN PATENT DOCUMENTS

| | | |
|---|---|---|
| DE | 19640807 | 9/1997 |
| EP | 0127947 | 12/1984 |
| EP | 0194105 | 10/1986 |
| EP | 0497021 | 5/1992 |
| EP | 1491135 | 12/2004 |
| EP | 1986543 | 11/2008 |
| FR | 2685865 | 1/1992 |
| JP | 4191642 | 7/1992 |
| JP | 7001273 | 1/1995 |
| JP | 10216115 | 8/1998 |
| JP | 11019074 | 1/1999 |
| JP | 2003194714 | 7/2003 |
| JP | 2003210438 | 7/2003 |
| JP | 2003275192 | 9/2003 |
| JP | 2004089546 | 3/2004 |
| JP | 2004148069 | 5/2004 |
| JP | 2004148070 | 5/2004 |
| JP | 2004248819 | 9/2004 |
| JP | 2004248820 | 9/2004 |
| JP | 2004290544 | 10/2004 |
| WO | WO9111137 | 8/1991 |
| WO | WO9200513 | 1/1992 |
| WO | WO9221281 | 12/1992 |
| WO | WO9309711 | 5/1993 |
| WO | WO9316629 | 9/1993 |
| WO | WO9403102 | 2/1994 |
| WO | WO9502358 | 1/1995 |
| WO | WO9512349 | 5/1995 |
| WO | WO9749330 | 12/1997 |
| WO | WO9817174 | 4/1998 |
| WO | WO9857577 | 12/1998 |
| WO | WO02062213 | 8/2002 |
| WO | WO2005009221 | 2/2005 |
| WO | WO2006097437 | 9/2006 |
| WO | WO2006097910 | 9/2006 |
| WO | WO2007013708 | 2/2007 |
| WO | WO2008020845 | 2/2008 |

OTHER PUBLICATIONS

Basak et al. "Support Vector Regression" Neural Information Processing —Letters and Reviews vol. 11, No. 10, Oct. 2007.*

Berhard et al. "Support Vector Machines and Kernel Algorithms" Mar. 20, 2002.*

Such, Hans Olaf; "Optoelectronic Non-invasive Vascular Diagnostics Using multiple Wavelength and Imaging Approach," Dissertation, (1998).

Ikeda, Kenji, et al.; "Improvement of Photo-Electric Plethysmograph Applying Newly Developed Opto-Electronic Devices," IEEE Tencon, pp. 1109-1112 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22$^{nd}$ Annual EMBS International Conference*, Chicago, Illinois; Jul. 23-28, 2000; pp. 2792-2795.

Aoyagi, T., et al.; "Pulse Oximeters: background, present and future," Neonatal Care, vol. 13, No. 7, pp. 21-27 (2000) (Article in Japanese—contains English summary of article).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Cyrill, D., et al.; "Adaptive Comb Filter for Quasi-Periodic Physiologic Signals," *Proceedings of the 25$^{th}$ Annual International Conference of the IEEE EMBS*, Cancun, Mexico, Sep. 17-21, 2003; pp. 2439-2442.

Aoyagi, Takuo; "Pulse oximetry: its invention, theory, and future," *Journal of Anesthesia*, vol. 17, pp. 259-266 (2003).

Itoh, K., et al.; "Pulse Oximeter," *Toyaku Zasshi* (Toyaku Journal), vol. 25, No. 8, pp. 50-54 (2003) (Article in Japanese—contains English summary of article).

Johnston, William S., et al.; "Effects of Motion Artifacts on helmet-Mounted Pulse Oximeter Sensors," 2 pgs. (2004).

Matsuzawa, Y., et al.; "Pulse Oximeter," *Home Care Medicine*, pp. 42-45 (Jul. 2004); (Article in Japanese—contains English summary of article).

Odagiri, Y.; "Pulse Wave Measuring Device," *Micromechatronics*, vol. 42, No. 3, pp. 6-11 (undated) (Article in Japanese—contains English summary of article).

Lutter, N., et al.; "Comparison of Different Evaluation Methods for a Multi-wavelength Pulse Oximeter," *Biomedizinische Technik*, vol. 43, (1998).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

\* cited by examiner

SYSTEM AND METHOD FOR ESTIMATING BLOOD ANALYTE CONCENTRATION

RELATED APPLICATIONS

This application claims priority to U.S. Provisional Application No. 61/072,293, filed Mar. 28, 2008, and is incorporated herein by reference in its entirety.

BACKGROUND

The present disclosure relates generally to medical devices and, more particularly, to non-invasive medical devices and methods used for determining blood analyte concentrations.

This section is intended to introduce the reader to various aspects that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices may have been developed for monitoring many such characteristics of a patient. Such devices may provide doctors and other healthcare personnel with the information they need to provide the best possible healthcare for their patients. As a result such monitoring devices have become useful in treating patients.

Non-invasive medical devices may be particularly useful and desirable, as they generally provide immediate feedback and do not traumatize a patient. Typically, non-invasive sensors may transmit electromagnetic radiation, such as light, through a patient's tissue. The light passed through the tissue may be selected to be of one or more wavelengths that may be absorbed and scattered by particular tissue constituents, such as blood, for example. The sensor may photoelectrically detect the absorption and scattering of the transmitted light in such tissue. One or more physiological characteristics may then be calculated based upon the amount of light absorbed and/or scattered.

One non-invasive technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, dynamic changes in amount and type of blood constituents in tissue, and/or the rate of blood pulsations corresponding to each heartbeat of a patient. However, nonlinearities may be introduced that may make it difficult to achieve accurate measurements. In particular, environmental factors and movement of the sensor relative to the measured tissue may affect measurement accuracy.

SUMMARY

Certain aspects commensurate in scope with the disclosure are set forth below. It should be understood that these aspects are presented merely to provide the reader with a brief summary of certain forms the embodiments might take and, these aspects are not intended to limit the scope of the disclosure. Indeed, the disclosure may encompass a variety of aspects that may not be set forth below.

In an embodiment, there is provided a method for non-invasively estimating blood analyte concentrations. The method for non-invasively estimating blood analyte concentration includes detecting light from a plurality of light sources and generating signals representative of observed absorption of the light from the plurality of light sources. Blood analyte concentrations are computed using support vector regression analysis of the generated signals.

In accordance with an embodiment there is provided a system for estimating blood analyte concentration. The system includes a sensor comprising a plurality of light sources and a detector configured to generate signals based on light from the plurality of light sources. The system also includes a monitor coupled to the sensor configured to receive the signals generated by the detector and estimate blood analytes using support vector regression (SVR) analysis. The estimated blood analyte concentration may then be output.

In accordance with an embodiment, a method of manufacturing a non-invasive medical device is provided. The method includes programming a non-invasive medical device to solve an support vector regression problem having a form:

$$y = \sum_i \alpha^{(i)} \kappa(w^{(i)}, x) + b,$$

where y is the blood analyte concentration and x represents the signals representative of the observed absorption of the light, $w^{(i)}$ represents the support vectors, k is a kernel and $\alpha$ and b are parameters. The programming of the non-invasive medical device includes devising a pretransform to avoid scale variances in observed data, selecting a kernel function k, gathering training data $x_t$ and $y_t$; performing minimization on training data $x_t$ and $y_t$ to obtain parameters $\alpha$, b and support vectors $w^{(i)}$ and testing a known non-training set of data $x_{nt}$. If the result of the test is sufficiently accurate, then the non-invasive medical device is programmed with the obtained parameters a and b, support vectors $w^{(i)}$, the selected kernel k, and the support vector regression problem having a form:

$$y = \sum_i \alpha^{(i)} \kappa(w^{(i)}, x) + b.$$

BRIEF DESCRIPTION OF THE DRAWINGS

Advantages of embodiments may become apparent upon reading the following detailed description and upon reference to the drawings in which.

DETAILED DESCRIPTION OF SPECIFIC EMBODIMENTS

Figure 1:
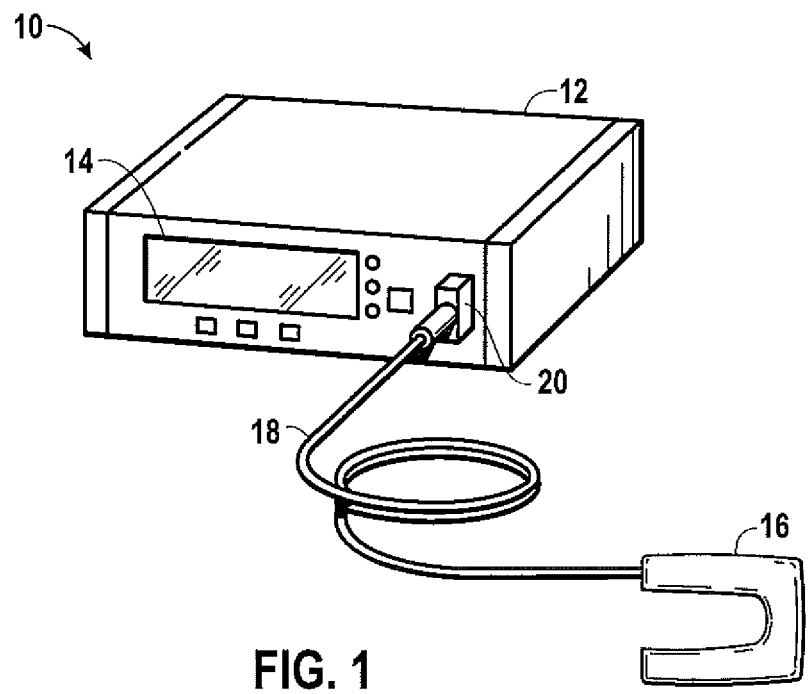
FIG. 1 illustrates a pulse oximetry system in accordance with an embodiment.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In order to overcome the effects of nonlinearities and to achieve accurate measurements, there is provided a system and method for estimating blood analyte concentrations using support vector regression (SVR). A support vector formulation allows for nonlinear effects to be captured, as will be discussed in greater detail below. Moreover, the use of the SVR formulation limits the intellectual "heavy lifting" required in algorithm design, as the optimization process "learns" the best way to measure through noise. Additionally, a high power computer is only needed to compute support vectors prior to implementation of the SVR method in a non-invasive medical device used to estimate blood analyte concentrations. Once computed, the support vectors may be programmed into the device used to estimate the blood analyte concentrations. Thus, the device used to estimate the blood analyte concentrations requires relatively little computing power, as it only performs multiplication and addition functions. Additionally, as faster processors and memory become cheaper, the support vector formulation may be scaled to provide more accurate estimations.

SVRs are excellent for non-parametric regression and for finding patterns below the cognitive threshold of humans. As will be discussed in detail below, the calibration of an SVR oximeter would work generally as follows:

1. Gather a lot of data of the form $\{(x_k, y_k)\}_{k=1}^n$, where $x_k$ is a vector of (multiple) red, IR, and/or other light signals over a small time window, and $y_k$ is the measured (by standardized technique) of the oxygen saturation over the same time window.

2. The SVR then generates a function $f(x)$ such that $f(x_k) \approx y_k$ for $k=1 \ldots n$, and such that $f$ is expressed as a linear combination of kernel functions:

$$f(x) = \alpha_0 + \sum_{j=1}^{m} \alpha_j K(Xk_j, x),$$

where K is the selected kernel function (which may depend on a few parameters.) While generating the function $f$ may be computationally challenging, representing the function $f$ and evaluating it for an arbitrary x (e.g., in an oximeter) is less challenging. The whole point of the using SVR is that it may be better at "learning" how to reject noise than any ad hoc heuristics created by humans. Moreover, it should be able to integrate a third (or fourth, etc.) wavelength signal into an estimator of saturation without much additional effort. Additionally, it should be noted that the saturation estimator described herein is not a drop-in replacement for least squares regression in the usual saturation estimator given by $i_k \approx \hat{b} + \hat{m} r_k$, where $i_k$ is a single IR measurement, and $r_k$ is a single measurement at the red wavelength.

Referring to the figures and turning initially to FIG. 1, a non-invasive medical device is illustrated in accordance with an embodiment and is generally designated by the reference numeral 10. The non-invasive medical device 10 may include a monitor 12 which may house hardware and software configured to compute various physiological parameters. The monitor 12 may be configured to operate as a pulse oximetry or multi-parameter monitor, such as those available from Nellcor Puritan Bennett L.L.C. and/or Covidien. The monitor 12 may include a display 14 to display the various physiological parameters. For example, the display 14 may display the pulse rate and the concentration of a blood analyte, such as, percent oxygen saturation of hemoglobin, for example. The display 14 may show the physiological parameters and calculated values in any appropriate manner. For example, the calculated values may be displayed numerically and/or as a waveform over time. Additionally, any notifications or alerts prompted by abnormal measurements, calculated values and/or other conditions may be displayed.

Figure 2:
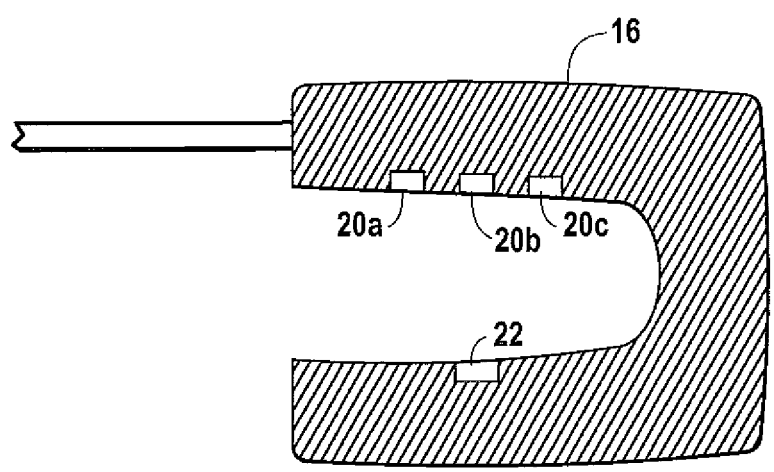
FIG. 2 illustrates a cross-sectional view of a sensor for the pulse oximetry system of FIG. 1 in accordance with an embodiment.

A sensor 16 may be communicatively coupled to the monitor 12 via a cable 18 and a connector 20. A cross-sectional view of the sensor 16 is illustrated in FIG. 2. As can be seen, the sensor 16 may have three emitters 20a-c capable of directing electromagnetic radiation, or light. Each emitter 20a-c may emit light at a unique or discrete wavelength. Specifically, the first emitter 20a may emit light in the red region of the electromagnetic spectrum, i.e., approximately 600 nm to 750 nm, the second emitter 20b may emit light in the infrared (IR) region of the electromagnetic spectrum i.e., approximately 750 nm to 1 mm, and the third emitter 20c may emit light in the near to mid IR region, i.e., approximately 750 nm to 40 micrometers. The emitters 20a-c may be any suitable emitter, such as LEDs, a broad spectrum emitter, or a scanning light source that incrementally emits across a broad spectrum of wavelengths, for example.

The sensor 16 may also include a detector 22. The detector 22 may include one or more photodetectors configured to detect light in the electromagnetic regions in which the emitters 20a-c operate. For example, in an embodiment, a silicon photodetector may be provided as well as an indium-gallium-arsenide photodetector, so that electromagnetic radiation in the red and infrared regions of the electromagnetic spectrum may be detected.

Figure 3:
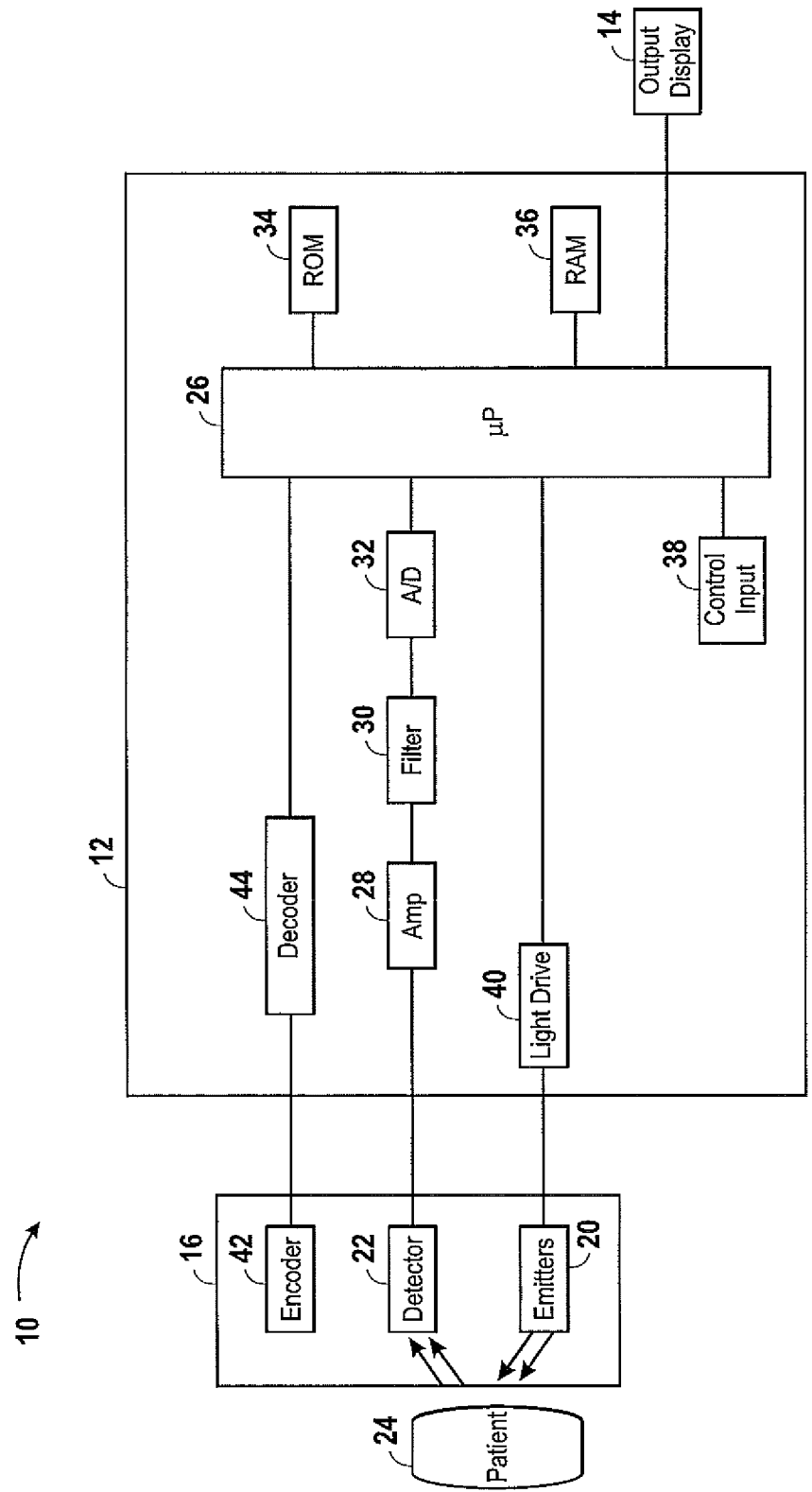
FIG. 3. illustrates a block diagram of the pulse oximetry system of FIG. 1 in accordance with an embodiment.

In response to detecting the electromagnetic radiation, the detector 22 may be configured to generate a signal corresponding to the detected light. The signal generated by the detector 22 may be provided to the monitor 12. FIG. 3 illustrates a block diagram of the non-invasive medical device 10 in accordance with an embodiment. It should be understood that the non-invasive medical device 10 is exemplary and an actual implementation may include more or fewer components as desired for a specific application for which the non-invasive medical device 10 is to be used. As illustrated, the monitor 12 includes a microprocessor 26 which receives the signal generated by the detector 22 after it has been amplified (amplifier 28), filtered (filter 30) and converted to a digital signal (A/D converter 32).

The microprocessor 26 may be configured to calculate the concentration of analytes in the blood, as well as various physiological parameters, characteristics, and/or other metrics of the patient 24 using algorithms programmed into the monitor 12. The microprocessor 26 may be connected to other component parts of the monitor 12, such as a ROM 34, a RAM 36, control inputs 38 and a light drive unit 40. The ROM 34 may be configured to store the algorithms used to compute the physiological parameters, characteristics, and/or metrics, and the RAM 36 may be configured to store the signals generated by the sensor 16 for use in the algorithms. The control inputs 38 may be provided to allow a user to interface with the monitor 12 and may include soft keys, dedicated function keys, a keyboard, and/or keypad type interfaces for providing parameters, data, and/or instructions to the monitor 12. In certain embodiments, the control inputs 38 may also include speech or tone recognition or other audio, remote, and/or hands-free command input type devices. The light drive unit 40 in the spectrophotometric monitor 12 may control the timing of the emitters 20.

Additionally, an encoder 42 and decoder 44 may be provided to calibrate the monitor 12 to the actual wavelengths emitted by the emitters 20. The encoder 42 may be a resistor for example, whose value corresponds to one or more of the emitter wavelengths so that proper coefficients stored in the monitor 12 may be selected. In another embodiment, the encoder 42 may be a memory device, such as an EPROM, that stores information, such as information related to the emitter wavelengths or the coefficients themselves, for example. Once the coefficients are determined by the monitor 12, they may be inserted into the algorithms in order to calibrate the calculations that are being performed by the system 10.

Support Vector Regression

As mentioned above, support vector regression is a technique for automated learning. That is, a set of calibration data denoted $\{x^{(k)}\}_k^n=1$, with corresponding responses $\{y^{(k)}\}_k^n=1$ measured by a reference technique is collected and provided to an algorithm which finds the optimal prediction of y from x. In the non-invasive medical device 10, x may represent the optical observations detected by detector 22, for example, possibly over a number of time steps and y may be the blood analyte concentration to be estimated (e.g., percent oxygen saturation).

The support vector regression may build a model of the form:

$$y = \sum_i \alpha^{(i)} \kappa(w^{(i)}, x) + b,$$

where K is a "kernel function" chosen by a practitioner and $w^{(i)}$, and $\alpha^{(i)}$ and b are discovered by calibrating the method to large amounts of data for which y has been measured by a reliable reference method, such as pulse oximetry measurements performed on a non-moving hand, for example. In the simplest formulation K is the simple dot product: $K(u,v)=u\cdot v$. Nonlinear effects can be captured while using a SVR model by using nonlinear kernels. For example, the following are valid kernels which capture nonlinear effects:

$K(u,v)=(u\cdot v+c)^k, K(u,v)=\tan h(cu\cdot v+\Theta),$
$K(u,v)=e^{-\|u-v\|_2^2/2\sigma^2}.$ Once the reference data is gathered, i.e., the observed x and the measured y, and the kernel is chosen, optimization techniques are used to find the support vector $w^{(i)}$, as well as the appropriate number of these vectors, and the $\alpha^{(i)}$ and b. The optimization problem is characterized by two features: the desired error of the ultimate model should be smaller than a given ε for the observed training data, and the vectors $w^{(i)}$ should be as "flat" as possible. This flatness may help avoid amplification of observation error in the estimation of y. From these two features, optimization theory tells us that the optimal support vectors $w^{(i)}$ will actually be vectors from the training data. There will be more such vectors for smaller ε. That is, a less accurate analyte estimating device will require less memory for fewer support vectors, while a more accurate analyte estimating device will require more memory.

For the purpose of measuring blood analyte concentrations, such as oxygen, for example, from observations of optical absorption at multiple wavelengths of multiple time steps, x is the vector of optical observations and y can be measured by a reference technique, such as DC oximetry of a blood draw or pulse oximetry on a non-moving hand, for example. The optical observations may be performed at three channels, red, IR, and mid IR. The posting rate may be one-thirtieth the sampling rate of the device, so that x has 90 elements:

$x=[red_1, red_2, \ldots, red_{30}, IR_1, IR_2, \ldots, IR_{30}, nIR_1, nIR_2, \ldots, nIR_{30}]^T.$ As such, the device may estimate y from 30 observations of each of the three channels. The x and y values are used to "train" the support vector machine. That is, they are used as reference vectors for learning how to estimate the concentration of the blood analyte, as discussed below.

Figure 4:
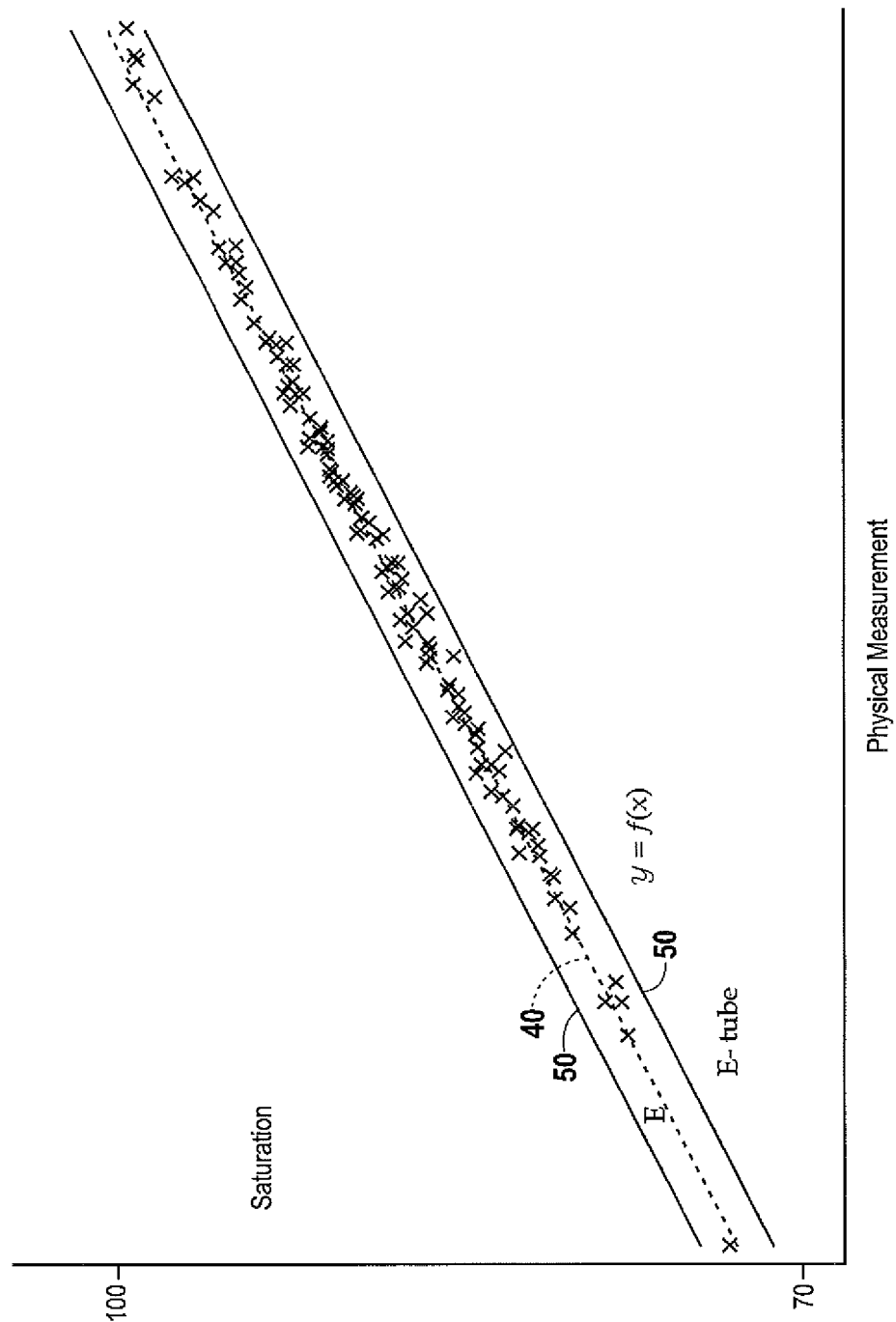
FIG. 4 illustrates a linear ϵ-tube for the function $f(w)=w \cdot x+b$.

After being trained on the calibration data, the support vector regression technique produces a function $f$ which should model the calibration data well: $y^{(k)} \approx f(x)$. If ε denotes the required accuracy of the device, the algorithm is considered a success if $|y^{(k)} - f(x^{(k)})| \leq \varepsilon$ for all k. Referring to FIG. 4, a linear function of the form $f(x)=w\cdot x+b$ is shown. Such a linear function is the simplest conceivable regression function. As can be seen, the ε-tube includes a line representing the linear function $f(x)=w\cdot x+b$, shown as line 48 and representing the blood analyte concentration y, with ε tube lines 50 on either side of the line 48. In FIG. 4, the horizontal axis represents the physical measurement and is to be imagined as a high dimensional vector space. The vertical axis represents the percent saturation of oxygen in hemoglobin and has a scale from 70% to 100%. The x's in FIG. 4 may represent optical observations or measurements taken by the non-invasive medical device 10 and each is constrained within the ε-tube. The linear formulation will be discussed in greater detail below.

Linear Formulation

Figure 5:
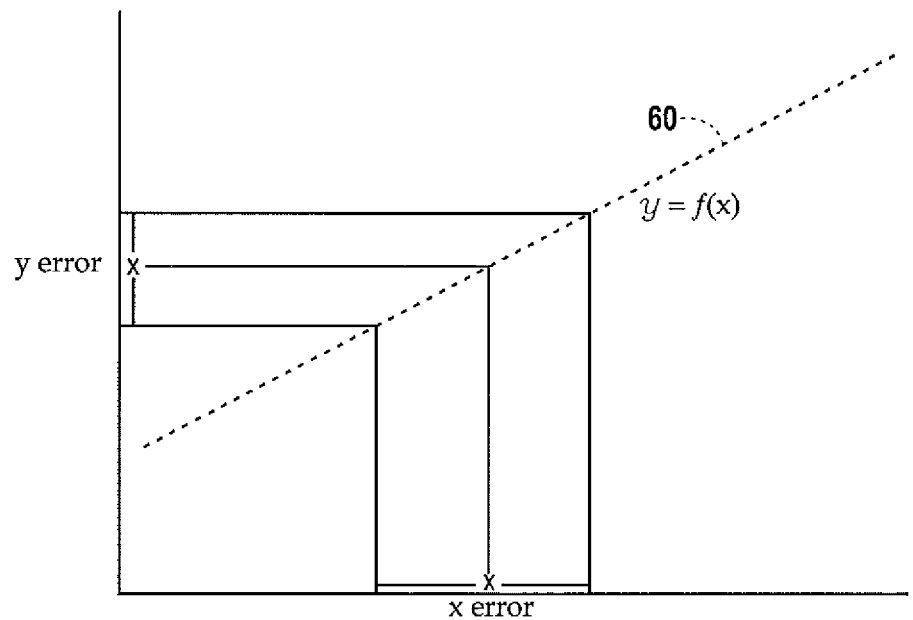
FIG. 5 illustrates an amount of uncertainty translated from observed data to measured data when a linear function has a slope less than one.
Figure 6:
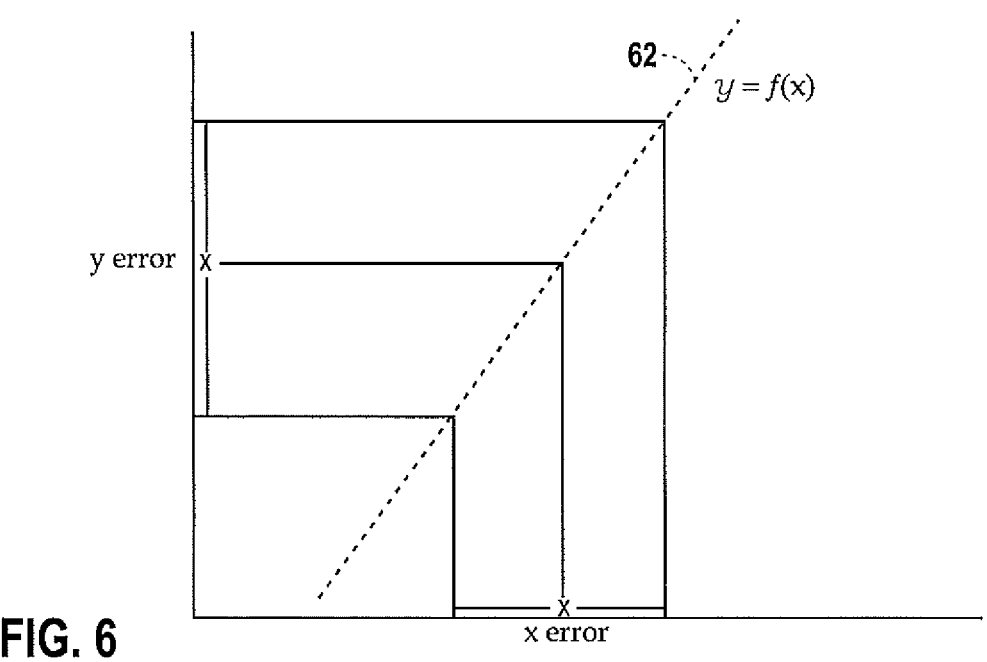
FIG. 6 illustrates an amount of uncertainty translated from observed data to measured data when a linear function has a slope greater than one.

The robustness of the algorithm is determined by the slope of the function and, as such, the vectors $w^{(i)}$ should be as flat as possible. FIGS. 5 and 6, show two linear functions 60 and 62 having different slopes. The linear function 60, illustrated in FIG. 5, is flatter or has a smaller slope than the linear function 62 of FIG. 6. Although the observed error in x is approximately the same in the two figures, because of the linear function 62 has a slope greater than one, there is possible amplification of the observation error in x in the measured parameters y. Thus, a linear function with smaller $\|w\|^2$ gives a more robust estimate of y because $\nabla_x y = w$. Stated differently, if x is measured with uncertainty $\Delta x$, uncertainty in the estimation of y is:

$y+\Delta y = f(x+\Delta x) = w\cdot x + w\cdot \Delta x + b.$

Assuming the data follow a linear relationship:

$\Delta y = w \cdot \Delta x = \|w\|_2 \|\Delta x\|_2 \cos \theta,$ where θ is the angle between the two vectors. Since we cannot control uncertainty in the optical observations, we would like $\|w\|^2$ to be small. Thus) combining the fitting requirement and the desire for robustness gives the best linear function as the solution to an optimization problem:

$$\min_{|y^{(k)}-(w\cdot x^{(k)}+b)|\le\varepsilon,\forall k} w\cdot w.$$

This is a constrained quadratic optimization problem for which stock algorithms exist. However, there may not exist a w, i.e., there is not ε tube which contains the data. The optimization problem may be designed to work around this complication by building some slack into the ε-tube requirement. For the present purposes the problem is assumed to be valid.

The first order necessary conditions, the Karush-Kuhn-Tucker Conditions (KKT Conditions), for a solution to this problem indicate that if w is optimal, then $$w = \sum_{k=1}^{n} \alpha^{(k)} x^{(k)},$$

for constants $\alpha^{(k)}$. Moreover, by complementarity, $\alpha^{(k)}=0$ if $|y^{(k)}-(w\cdot x^{(k)}+b)|<\varepsilon$, i.e., $\alpha^{(k)}$ is nonzero only if $|y^{(k)}-(w\cdot x^{(k)}+b)|=\varepsilon$. The calibration vectors $x^{(k)}$ for which a $\alpha^{(k)}\ne 0$ (which contribute to w) are called "support vectors." The regression vector is, is a linear combination of the support vectors, and the support vectors are training vectors $x^{(k)}$ which lay on the ε-tube, not strictly within it.

By linearity, the linear function may be re-written as $$f(x) = w \cdot x + b$$

$$= \sum_{k=1}^{n} \alpha^{(k)} x^{(k)} \cdot x + b.$$

Nonlinear Expansion

The linear formulation set forth above may be expanded to the case of nonlinear functions $f$. Imagine a function $\phi$: $\mathbb{R}^m \to \mathbb{R}^l$, which carries the nm-dimensional measurement vector x to a higher dimensional space. The idea is to replicate the linear formulation set forth above in the space $\mathbb{R}^l$ after transforming the physical measurements. That is, find the l-dimensional vector w of minimal norm subject to: $|y^{(k)}-(w\cdot\Phi(x^{(k)})+b)|\le\varepsilon,\forall k$.

As above, $$f(x) = w \cdot \Phi(x) + b$$

$$= \sum_{k=1}^{n} \alpha^{(k)} \Phi(x^{(k)}) \cdot \Phi(x) + b.$$

The $\alpha^{(k)}$ are nonzero for support vectors in l-space.

This formulation may be simplified by the use of the "kernel trick,"

The kernel function may be defined by $K(z,x)=\Phi(z)\cdot\Phi(x)$.

Use of the kernel allows the re-writing of the function as $$f(x) = \sum_{k=1}^{n} \alpha^{(k)} \kappa(x^{(k)}, x) + b.$$

The kernel simplifies the equation and the computation, as it is often more simple (requires less computation time) to compute K(z,x) than to explicitly compute $\Phi(z)\cdot\Phi(x)$. This allows for minimization in the high dimensional feature space while doing all computations in the lower dimensional observations space. For example, $K(z,x)=(z\cdot x)^2$ is a valid kernel, as it corresponds to a transformation θ which take $R^m$ to $R^{m^2}$. For even modest m, the computational savings are significant. In some cases, the feature space corresponding to a kernel is infinite dimensional. There are results, such as Mercer's Theorem, which guarantee a function is a kernel without identifying the transform θ. Also, products, positive linear combinations and integrals of kernels are also kernels. There are even kernel-like functions which can be shown not to be truly kernels, but which work well in practice for support vector regression. Support vector regression and classification are widely used for machine learning, weather prediction, etc., and, as such, high quality software written in common high level programming languages such as C++ is readily available. Furthermore, a kernel is more descriptive than its corresponding transform θ. For example, the kernel $K(z,x)=z\cdot x+(z\cdot x)^2$, clearly captures linear and quadratic relationships among the physical measurements, whereas any description of the corresponding transform may not present the relationship as clearly.

Support Vectors in Non-Invasive Medical Devices

Figure 7:
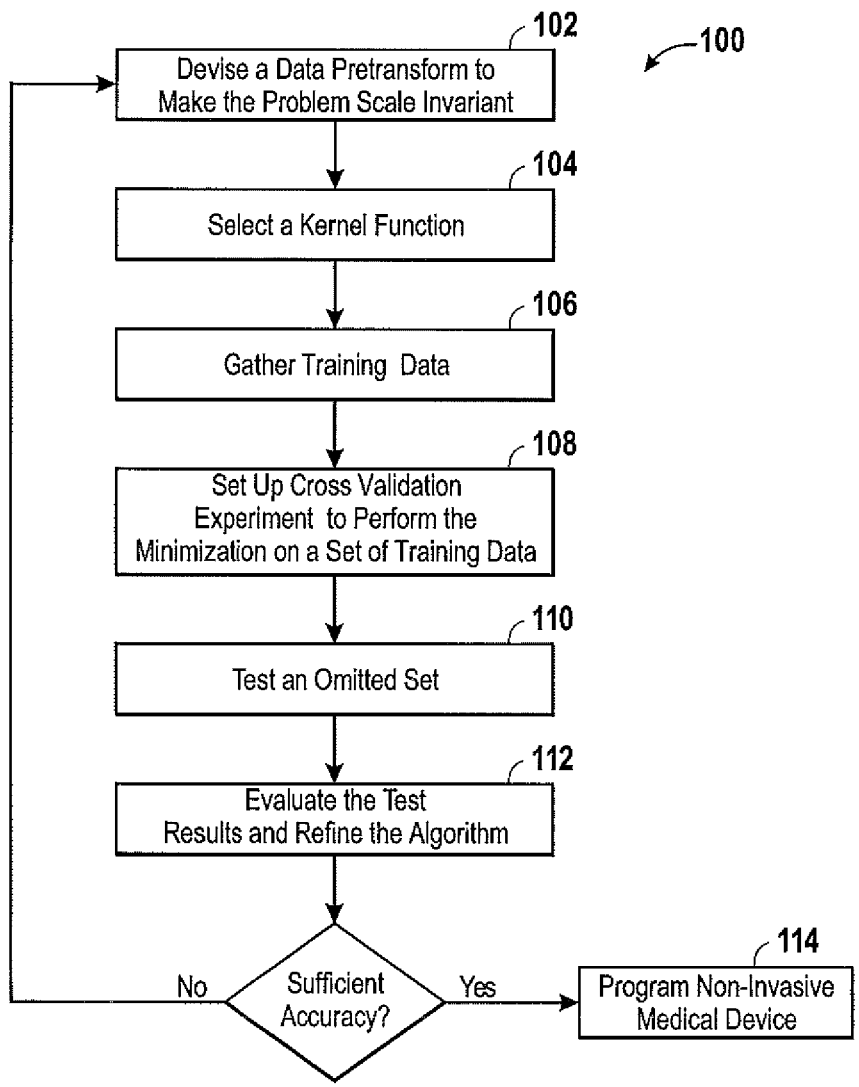
FIG. 7 is a flow chart illustrating a method of manufacturing a non-invasive device to estimate blood analyte concentration using support vector regression.

A flow chart illustrating a method of manufacturing non-invasive medical devices to use support vector regression is shown in FIG. 7 and may generally be referred to by the reference number 100. As indicated at block 102, a data pretransform is devised to make the problem scale invariant. That is, for example, in pulse oximetry, blood analyte concentrations are often radiometric and should remain unchanged by uniform changes in measurements, e.g., a doubling of all the optical measurements. This allows for the estimations of saturation to remain unchanged even if the optical source is made brighter, for example. Thus, we have $f(x)=f(cx)$, for any nonzero positive constant c. One way to achieve this property is to project the data down to the sphere, i.e., to perform the transform $g(x)=x/\|x\|_2$ before using the optical data. In this case, one degree of freedom has been lost so the last element of the output of g may be ignored.

Usually, data are transformed before being fed to an SVR. One common Technique is "studentization" wherein the sample mean is subtracted from the data and the data are divided by their sample standard deviation. This may help place the data on the correct scale. Any preprocessing transform on the data may be rolled into the regression function which may be used in the oximeter. That is, if data are transformed by $\tilde{x}_k=\psi(x_k)$, then fed to the SVR process, the same preprocessing may be performed in the oximeter. Thus, the raw data x observed by the oximeter is transformed by $\tilde{x}_k=\psi(x_k)$ before being passed to the SVR function. Note that it is in the preprocessing and kernel selection that some structure may be imposed on the solution based on the physics of oximetry. For example, since overall scale of the observed red and IR signals should be irrelevant to the measurement of saturation, e.g., the peak-trough amplitude of both pleth signals could double without a change in saturation, the restriction may be imposed on the SVR solution, by selecting appropriate transform and kernel. For example, a log transform of the optical data may be used and then a sample mean subtracted. Or, the red and IR signals may be combined together, taking their ratio and only passing the quotient to the SVR process. Moreover, the kernel and the transformation may be designed with recognition that the vector of optical data could be from any section of the pleth signal (and not e.g., timed to start from a trough in the pleth.

After the preprocessing transform is selected, a kernel function is selected, as indicated as block 104. The following nonlinear kernels are available for use in most support vector regression packages:

$$K(u,v) = (u \cdot v + c)^k, \quad \text{(Polynomial)}$$

$$K(u,v) = \tan h(cu \cdot v + \Theta), \quad \text{(Sigmoidal)}$$

$$K(u,v) = e^{-\|u-v\|^2/2\sigma^2}. \quad \text{(Gaussian)}$$

Training data is then gathered, as indicated at block 106. A large amount of training data is readily available, however, saturation data from a second hand should be converted to equivalent rat-rat or the algorithm will be trained on a particular R-cal. Moreover, all training data should be subject to the same preprocessing filters, as the method outlined above groups successive observations together. The collected data should include normal and challenging conditions, such as stray light, decoupling, movement tapping, scratching, etc.

Some kernel and transform choices may lead to a more or less forgiving function $f$ with regard to observed data unlike anything in the training set. This is the reason for gathering data that includes a variety of conditions. However, the SVR oximeter should be able to recognize data that may be classified as outliers and provide an appropriate response. For example, the oximeter may be configured to raise an alarm when an outlier is detected. Alternatively, the oximeter may simply use a different technique for measuring/estimating saturation.

In a traditional oximeter based on linear regression, a regression coefficient $\hat{m}$ for the approximation $i_k \approx \hat{b} + \hat{m} r_k$, is found and used with a lookup table based on the wavelengths of the red and IR light to transform the slope m into a saturation estimate y. It is not clear how the SVR oximeter would deal with the slight differences in wavelength which are present in commercial oximetry sensors. It is not obvious a priori that an SVR function $f$ trained on one set of date $\{(x_k, y_k)\}_k^n = 1$, gathered using one particular choice of red and IR wavelengths, could easily be used with a sensor using slightly different wavelengths. There are a few possibilities for dealing with this issue:

1. Generate a SVR function $f$ for each possible choice of red and IR wavelength, and have the oximeter detect, via R-cal techniques, what wavelengths are used in a particular sensor.

2. Devise preprocessing transforms which depend on the wavelengths used by the sensor. This may be difficult from an engineering standpoint and the extra parameters may introduce the possibility of overfitting. The use of this option would be tied to the choice of preprocessing transform and kernel, and, as noted above, the physics of oximetry (e.g., the different absorptive coefficients of hemoglobin at the different wavelengths) may be translated into an appropriate transform in this case. For example, if only ratiometric data were fed into the SVR function, the ratiometric data may be multiplied by the ratio of particular absorption coefficients for the wavelengths present in the sensor to correct for said different absorption coefficients. If a log transform were used, a linear offset depending on the wavelengths seems appropriate. In this case, data from all possible combinations of sensor wavelengths may be used in the collection of data, $\{(x_k, y_k)\}_k^n = 1$, for training and evaluating the SVR function.

3. Train the SVR function on the preimage of saturation under a R-cal-like transform. That is instead of using the SVR technique to find $f$ such that $f(x_k) \approx y_k$, one would instead use the SVR technique to find g such that $g(x_k) \approx z_k$, where $l(z_k, \lambda_i, \lambda_r) = y_k$, and where l is the R-cal transform which maps some kind of slope estimate and the wavelengths of light in the sensor ($\lambda_i$ and $\lambda_r$) to the saturation. The R-cal transforms currently used in linear-regression type oximeters may be used for this purpose. In this case as well, data from all possible combinations of sensor wavelengths may be used in the collection of data, $\{(x_k, y_k)\}_k^n = 1$, for training and evaluating the SVR function.

After training, a cross-validation experiment may be set tip to perform minimization on the training data and test data, as indicated in block 108 and 110. As mentioned above, this requires a relatively heavy amount of computing and may require a significant amount of time depending on the computational power available. The results are evaluated and refinements are made, as indicated at block 112, and then the process may be repeated until a desired level of accuracy is achieved. As stated above, the desired level of accuracy is achieved when the desired error on the test data is less than the given $\epsilon$ of the observed training data. Once the support vectors $w^{(i)}$ are found, they may be programmed into the nonlinear device 10 along with the selected kernel k, and parameters b and $\alpha^{(i)}$, as indicated at block 114.

Any practical SVR oximeter would have some engineering constraints, particularly memory and computational power. Moreover, the design of an oximeter would dictate certain accuracy requirements (e.g., ±3% accuracy during periods of no interference, ±6% during periods of moderate interference, etc.) There is, unfortunately, no a prior guarantee when constructing an SVR function that the number of support vectors (which essentially "describe" the function $f$ and which would have to be held in memory in the SVR oximeter) is sufficiently small or that the accuracy of the function $f$ is below a certain level even for the training data. For this reason, the calibration procedure may be performed only to produce an SVR function $f$ which is totally useless for engineering reasons (note that higher accuracy SVR functions usually require a greater number of support vectors, i.e., more memory). A cross validation may be performed based on the presumption that the accuracy of the training data is greater than the accuracy of the data used for the cross validation when using the SVR function. In the even this is not true, some changes may be made and the calibration re-run.

Easily conceivable changes and refinements include:
1. Choice of the number and identity of the wavelengths of light used.
2. Choice of the number of contiguous observations to aggregate into a vector to feed to the SVR process.
3. Choice of any preprocessing transform.
4. Choice of the kernel.
5. Choice of any parameters in the kernel. The SVR techniques may be highly sensitive to the proper choice of these parameters. For example, in the commonly used Gaussian kernel, $$K(u, v) = e^{-\|u-v\|_2^2/2\sigma^2},$$

The variance term $\sigma^2$ may be selected, but the choice may not be made independently of the choice of preprocessing transform. Similarly, the choice of c and k for the polynomial kernel, the choice of c and θ for the sigmoidal.

6. Choice of optimization technique for fining the SVR function.

7. Choice of loss function for the SVR technique. As the loss functions other than the ϵ-insensitive may result in too many support vectors, the ϵ-insensitive loss function may be selected.

The refinement process may consist of some amount of local refinement of the kernel parameters and some parameters in a set preprocessing transform. The local optimization may be performed without any human intervention and is naively parallelizable by a grid search (a cluster of computers could each explore a small area of parameter space, then the results would be combined). Changes to the kernel choice, or choice of preprocessing transform or choice of wavelengths used is a higher-level optimization procedure which may be less easy to automate.

Figure 8:
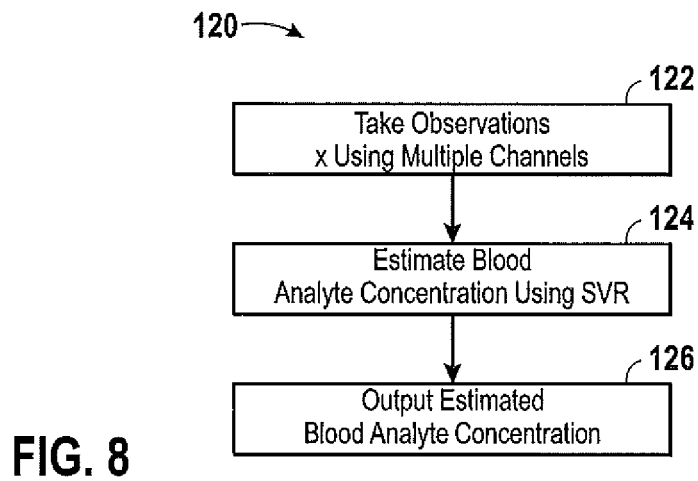
FIG. 8 is a flow chart illustrating the method of operation for a non-invasive medical device configured to estimate blood analyte concentration using support vector regression.

The programming of the non-invasive medical device 10 with the support vectors $w^{(i)}$, the selected kernel k; and parameters b and $\alpha^{(i)}$, allow for the device 10 to estimate the blood analyte concentrations using the support vector regression. FIG. 8 is a flow chart illustrating the method 120 of estimation of the blood analyte concentration by a non-invasive medical device using support vector regression. The method 120 begins with the non-invasive medical device 10 taking observations x using multiple channels, as indicated at block 122. Specifically, as discussed above, the non-invasive medical device 10 takes observations x using three emitters 22 having unique wavelengths. These observations x are then used to estimate blood analyte concentrations using support vector regression (SVR), as indicated at block 124. As discussed above, this includes insetting the observation x into the equation having the form $$y = \sum_i \alpha^{(i)} \kappa(w^{(i)}, x) + b,$$

to solve for y. Once y is known, it is output as the blood analyte concentration, as indicated at block 126. Specifically, it may be output to the display 14 of the non-invasive medical device 10.

In an embodiment, the computed y and observed x may be included in subsequent iterations of the support vector regression analysis. In particular, the computed y and observed x, may be used in subsequent estimations of y based on subsequent observations of x. Thus, the non-invasive medical device 10 may be configured to "learn" as it implements the SVR function.

While the disclosure may be conducive to various modifications and alternative forms, embodiments have been shown by way of example in the drawings and have been described in detail herein. However, it should be understood that the disclosure is not intended to be limited to the particular embodiments disclosed. Indeed, the present disclosure may not only be applied to measurements of blood oxygen saturation, but also for the measurement and/or analysis of other blood constituents using principles of pulse oximetry. For example, using the same, different, or additional wavelengths, the present disclosure may be utilized for the measurement and/or analysis of carboxyhemoglobin, met-hemoglobin, total hemoglobin, intravascular dyes, and/or water content, among many different physiological parameters. As such, the disclosure is to cover all modifications, equivalents, and alternatives falling within the spirit and scope of the disclosure as defined by the following appended claims.

What is claimed is:

1. A system for estimating blood analyte concentration comprising:
   a sensor comprising:
      a plurality of light sources configured to operate at different wavelengths; and
      a detector configured to generate signals based on light from the plurality of light sources; and
   a monitor coupled to the sensor configured to:
      receive the signals generated by the detector;
      determine the different wavelengths at which the plurality of light sources operate;
      select a support vector regression function for the different wavelengths at which the plurality of light sources operate;
      estimate blood analyte concentration using the selected support vector regression function in a support vector regression analysis of the received signals; and
      output the estimated blood analyte concentration.

2. The system of claim 1, wherein the plurality of light sources comprises three light sources operating at different wavelengths.

3. The system of claim 2, wherein the three light sources comprise:
   a first light source operating in the red region of the electromagnetic spectrum; and
   second and third light sources operating in the IR region of the electromagnetic spectrum.

4. The system of claim 1, wherein the monitor is configured to estimate the blood analyte concentration using an equation having the form $$y = \sum_i \alpha^{(i)} \kappa(w^{(i)}, \chi) + b,$$

where y is the blood analyte concentration and η represents the signals generated by the detector, the monitor comprising a memory configured to store support vectors $w^{(i)}$, a kernel k, and calibration parameters α and b.

5. The system of claim 4, wherein the kernel k a nonlinear kernel.

6. A method for non-invasively estimating blood analyte concentration comprising:
   operating a plurality of light sources at different wavelengths;
   detecting light from the plurality of light sources;
   generating signals representative of observed absorption of the light from the plurality of light sources;
   determining the different wavelengths at which the plurality of light sources are operating;
   selecting a support vector regression function for the different wavelengths at which the plurality of light sources are operating; and
   estimating blood analyte concentration using the selected support vector regression function in a support vector regression analysis of the generated signals.

7. The method of claim 6, wherein the estimating blood analyte concentration comprises solving for an equation having a form:

$$y = \sum_i \alpha^{(i)} \kappa(w^{(i)}, \chi) + b,$$

where y is the blood analyte concentration and x represents the signals representative of the observed absorption of the light, $w^{(i)}$ represents the support vectors, k is a kernel, and α and b are calibration parameters.

8. The method of claim 6, wherein operating the plurality of light sources comprises operating three light sources comprising a first light source operating in the red region of the electromagnetic spectrum, and second and third light sources operating in the infrared region of the electromagnetic spectrum.

9. The method of claim 7, wherein the kernel is a polynomial kernel.

10. The method of claim 7, wherein the kernel is a nonlinear kernel.

11. The method of claim 7, wherein the kernel is a sigmoidal kernel.

12. The method of claim 7, wherein the kernel is a Gaussian kernel.

13. A monitor comprising:
a memory configured to store one or more support vector regression functions for different wavelengths;
a processor configured to receive signals generated by a sensor, determine different wavelengths at which a plurality of light sources within the sensor operate, select a support vector regression function for the different wavelengths at which the plurality of light sources operate, and estimate blood analyte concentration using the selected support vector regression function in a support vector regression analysis of the received signals; and
a display configured to display the estimated blood analyte concentration.

14. The monitor of claim 13, wherein the plurality of light sources comprises three light sources operating at different wavelengths.

15. The monitor of claim 14, wherein the three light sources comprise a first light source operating in the red region of the electromagnetic spectrum, and second and third light sources operating in the IR region of the electromagnetic spectrum.

16. The monitor of claim 14, wherein the monitor is configured to estimate the blood analyte concentration using an equation having the form $$y = \sum_i \alpha^{(i)} \kappa(w^{(i)}, \chi) + b,$$

y is the blood analyte concentration and η represents the signals generated by the sensor, and the memory is configured to store support vectors $w^{(i)}$, a kernel k, and calibration parameters α and b.

17. The monitor of claim 16, wherein the kernel k is a nonlinear kernel.

18. The monitor of claim 16, wherein the kernel k is a polynomial kernel.

19. The monitor of claim 16, wherein the kernel k is a sigmoidal kernel.

20. The monitor of claim 16, wherein the kernel k is a Gaussian kernel.

* * * * *